United States Patent
Zoboyan et al.

(10) Patent No.: US 9,869,646 B2
(45) Date of Patent: Jan. 16, 2018

(54) VIEW TRIGGERING FOR RADIATION IMAGING SYSTEM

(71) Applicant: Analogic Corporation, Peabody, MA (US)

(72) Inventors: Sevag M. Zoboyan, Wakefield, MA (US); Edmund Alterio, Natick, MA (US); Justin A. Cianci, Somerville, MA (US); David Vacca, Salem, NH (US)

(73) Assignee: ANALOGIC CORPORATION, Peabody, MA (US)

( * ) Notice: Subject to any disclaimer, the term of this patent is extended or adjusted under 35 U.S.C. 154(b) by 447 days.

(21) Appl. No.: 14/682,461

(22) Filed: Apr. 9, 2015

(65) Prior Publication Data

US 2016/0299088 A1 Oct. 13, 2016

(51) Int. Cl.
*G01N 23/04* (2006.01)

(52) U.S. Cl.
CPC .................. *G01N 23/046* (2013.01)

(58) Field of Classification Search
None
See application file for complete search history.

(56) References Cited

U.S. PATENT DOCUMENTS

| | | | | |
|---|---|---|---|---|
| 6,639,965 B1 * | 10/2003 | Hsieh | ..................... | A61B 6/032 378/15 |
| 7,684,537 B2 * | 3/2010 | Imai | ..................... | A61B 6/405 378/16 |
| 2005/0111623 A1 * | 5/2005 | Bruder | ................... | A61B 6/032 378/95 |
| 2011/0110486 A1 * | 5/2011 | Bouhnik | ................ | A61B 6/032 378/8 |

* cited by examiner

*Primary Examiner* — Hoon Song
(74) *Attorney, Agent, or Firm* — Cooper Legal Group, LLC

(57) ABSTRACT

Among other things, one or more techniques and/or systems are described for triggering a radiation imaging system to perform data acquisition. A radiation imaging system may comprise a rotating gantry configured to rotate a radiation source and a detector array about an object to generate an image(s) of the object. A data acquisition system is configure to integrate charge that has accumulated during a period of time. A temporal length between integrations (e.g., an integration period) is adjusted based upon a desired number of total integrations to be performed during the revolution, changes in the rotational speed of the rotating gantry during the revolution, and/or a collective integration time for integrations already performed during the revolution.

20 Claims, 8 Drawing Sheets

VIEW TRIGGERING FOR RADIATION IMAGING SYSTEM

BACKGROUND

The present application relates to the field of radiation imaging systems. It finds particular application with the triggering of a data acquisition system of a radiation imaging system that uses charge integrating detector arrays to measure radiation photon flux rates at a detector cell. More particularly, it relates to adjusting an integration period of one or more charge integrating detector cells on the fly during a revolution of the detector array relative to an object under examination.

Today, radiation imaging systems such as computed tomography (CT) systems, single-photon emission computed tomography (SPECT) systems, projection systems, and/or line-scan systems, for example, are useful to provide information, or images, of interior aspects of an object under examination. Generally, the object is exposed to radiation comprising photons (e.g., x-rays, gamma rays, etc.), and an image(s) is formed based upon the radiation absorbed and/or attenuated by interior aspects of the object, or rather an amount of radiation photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation imaging systems typically comprise a detector array having one or more detector cells. Respective detector cells are configured to indirectly or directly convert radiation photons impingent thereon into electrical charge which is used to generate an electrical signal. The detector cells are typically "charge integrating" or "photon counting" type detector cells (e.g., the radiation imaging system operates in charge integrating mode or photon counting mode).

Charge integrating detector cells, also referred to as energy integrating detector cells, are configured to integrate the electrical charge generated over a period of time (e.g., at times referred to as a integration period or view) to generate a signal that is proportional to an incoming radiation photon flux rate at a detector cell. A tick fence is often used to define the integration period. The tick fence comprises physical markers that are disposed on a stationary gantry. As the rotating gantry rotates, the data acquisition system encounters the physical markers, which triggers the data acquisition system to perform an integration (e.g., readout the charge that has accumulated on respective detector cells and reset the detector cells). An integration period refers to the timespan between integrations of the detector cells. Within a given sector or segment of a revolution of the rotating gantry, there is a static number of integration periods that is defined by the number of physical markers within the sector. Typically, the markers are spaced uniformly over the revolution and thus each integration period represents a defined arc length of the rotation.

SUMMARY

Aspects of the present application address the above matters, and others. According to one aspect, a method for triggering a radiation imaging system to perform integrations, where a revolution of a rotating gantry of the radiation imaging system is divided into a plurality of sectors, is provided. The method comprises, for a first sector of the revolution, a first rotational period is determined. A first integration period is determined based upon the first rotational period. One or more integrations are triggered during the first sector based upon the first integration period. The method also comprises, for a second sector of the revolution, a second rotational period is determined. A second integration period is determined based upon the second rotational period. The second integration period is different than the first integration period. One or more integrations are triggered during the second sector based upon the second integration period.

According to another aspect, a method for triggering a radiation imaging system to perform data acquisition is provided. The method comprises determining a desired total number of integrations for a revolution of a rotating gantry. A first integration period between integrations for a sector is determined based upon a rotational period of the rotating gantry at a start of the sector. At a defined location in the revolution, a collective integration time of integrations performed from the start of the revolution may be determined. A second integration period between integrations for a second sector is determined based upon the collective integration time.

According to yet another aspect, a radiation imaging system is provided. The radiation imaging system comprises a radiation source. The radiation imaging system comprises a detector array. The detector array comprises one or more detector cells configured to accumulate charge generated responsive to impinging radiation emitted by the radiation source. The radiation imaging system comprises a rotating gantry configured to rotate the radiation source and the detector array. The radiation imaging system comprises a data acquisition system configured to integrate the charge that has accumulated during a view. An integration period between integrations is adjusted during a revolution of the rotating gantry based upon a number of integrations remaining to be performed and a collective integration time of integrations performed during a first portion the revolution.

Those of ordinary skill in the art will appreciate still other aspects of the present application upon reading and understanding the appended description.

FIGURES

The application is illustrated by way of example and not limitation in the figures of the accompanying drawings, in which like references generally indicate similar elements and in which.

DESCRIPTION

Figure 1:
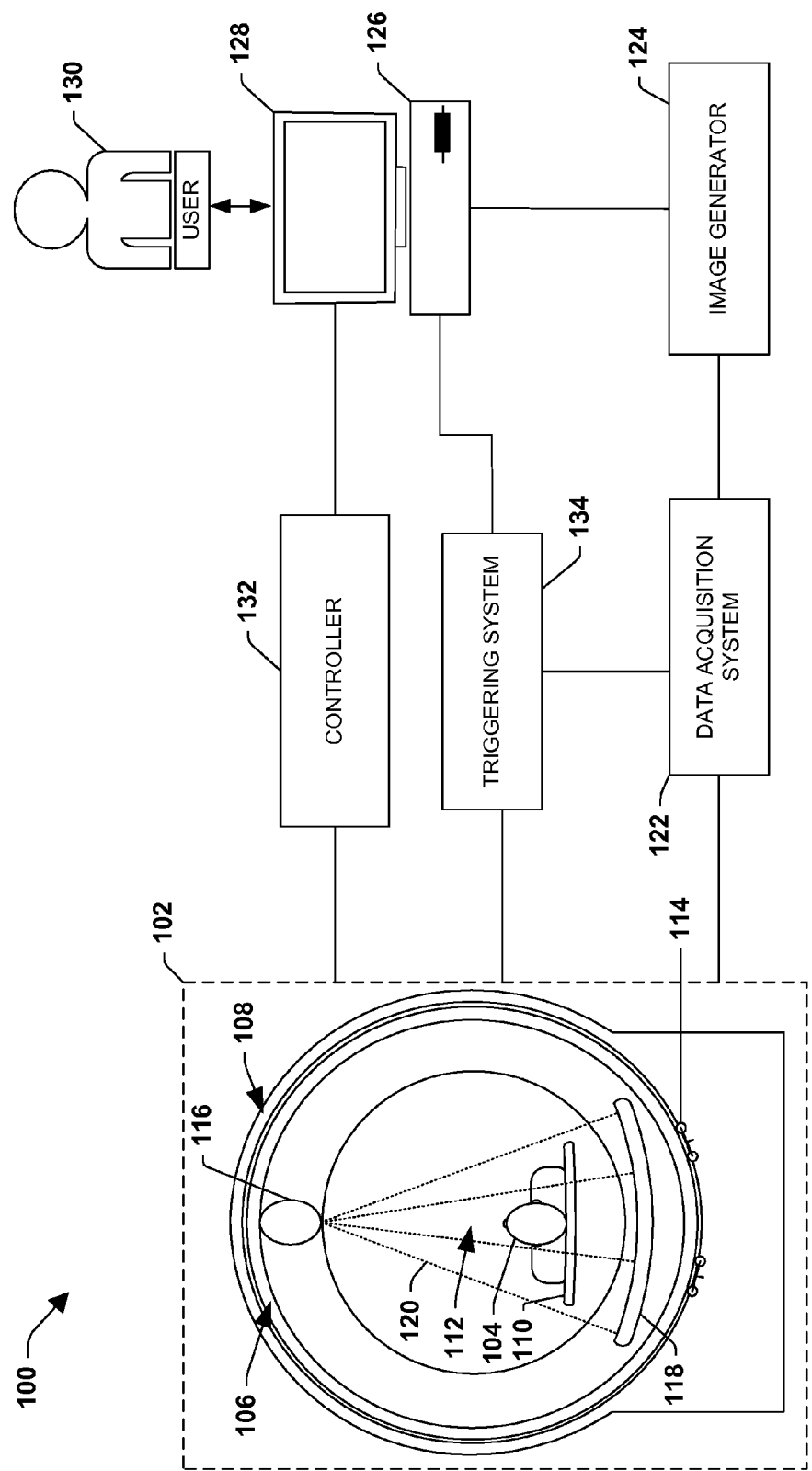
FIG. 1 illustrates an example environment of a radiation imaging system.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Physical markers, such as tick fences, have traditionally been used to trigger integrations of a radiation detector array because the physical markers help ensure that a defined number of integrations occur per period. Moreover, the physical markers can be manufactured to enable respective integration periods (e.g., views) to represent a substantially same arc length of a revolution. For example, respective integration periods may represent one quarter of one degree of a revolution.

Although triggering integrations based upon physical markers has proven successful, there are challenges to using physical markers. For example, tick fences may be expensive, difficult to mechanically align, susceptible to dust, susceptible to damage from regular service, and/or susceptible to vibration errors affecting position accuracy.

Accordingly, a radiation imaging system, such as a computed tomography (CT) system, comprising a data acquisition system that may be triggered by a combination of location-based markers and synthesized (e.g., virtual) triggers is provided for herein. A triggering system of the radiation imaging system may comprise one or more markers, such as apertures, fins, etc., that are positioned along the stationary gantry and/or the rotating gantry and are configured to define sectors of a revolution. For example, 18 markers may be spaced along a 360 degree (°) revolution. In some embodiments, respective markers are spaced equidistant long the 360° revolution and thus respective sectors defined between two markers may represent about a 20° sector (e.g., arc segment) of the revolution. In other embodiments, the markers may be spaced at non-uniform locations along the 360° revolution, and thus some sectors may represent a larger arc segment than other sectors.

The markers may be used to trigger the data acquisition system to perform an integration and/or may be used to determine a rotational period of the rotating gantry. For example, a first marker may be used to trigger an integration and to determine a rotational period of the rotating gantry for the first sector while other markers may be merely used to determine a rotational period for respective other sectors. As another example, a second marker may be used to determine a rotational period but not used to trigger an integration. Markers used to both trigger an integration and determine a rotational period of the rotating gantry may be referred to herein as "home markers".

The rotational period for a sector may be determined using a plurality of techniques. For example, in some embodiments, the rotational period for a sector is determined by measuring the amount of time it took for the rotating gantry to complete one full revolution relative to the marker. In still other embodiments, the rotational period for a sector is determined by measuring the amount of time it took for the rotating gantry to rotate through a portion of the revolution (e.g., one or more sectors of the revolution). In still other embodiments, the rotational period for a sector is determined by measuring an instantaneous speed of the rotating gantry (e.g., at the marker).

The triggering system may further use synthesized triggers to trigger the data acquisition system to perform additional integrations (e.g., not triggered by the home marker(s)). While a physical trigger is initiated responsive to identifying a home marker along a revolution, synthetic triggers are initiated responsive to a defined period of time having lapsed since a last integration. A temporal distance between such triggers defines an integration period, which is also referred to as a view and represents the data collected over an arc segment of the revolution. Thus, the synthetic triggers are temporally spaced apart by the integration period.

A number of synthesized triggers for a sector of a revolution may depend upon a desired number of views during the revolution. For example, the radiation imaging system may be designed to perform 720 views per revolution. Thus, there are 720 integrations within the revolution because respective integrations represent one view. If 18 markers are spaced equidistant along a 360 degree revolution, the desired number of integrations per sector is 65. Within a first sector, one of these integrations may be triggered by a home marker and the other 64 integrations may be triggered by synthesized triggers. Within the other sectors, respective (e.g., all) integrations may be triggered by synthesized triggers. The temporal spacing of these synthesized triggers may be a function of the rotational speed of a rotating gantry. For example, assume that the rotating gantry rotates at 60 revolutions per minute (RPM). If the sectors are uniformly spaced, each of the 18 sectors approximately corresponds to a 55.55 millisecond (ms) portion of the revolution. In such a scenario, to perform 65 integrations per sector, the synthesized triggers are spaced apart, in time, by approximately 854.61 microseconds (μs). Thus, the integration period is approximately 854.61 microseconds.

It may be appreciated that during a revolution of the rotating gantry, mechanical errors and/or an imbalance in the rotating gantry, for example, may cause the rotational speed of the rotating gantry to vary during a revolution. Thus, within a given sector of the revolution, the rotating gantry may rotate faster or slower than anticipated. For example, instead of a sector corresponding to a 55.55 millisecond portion of the revolution, it may correspond to a 53.525 millisecond portion of the revolution.

In some embodiments, to facilitate achieving the desired total number of integrations per sector and/or revolution, for example, the integration period between integrations is adjusted on-the-fly based upon a rotational speed, or rotational period, of the rotating gantry. For example, as will be described in more detail below, at a start of a sector, as indicated by a marker, a rotational period for the sector may be determined (e.g., where the rotational period corresponds to the amount of time that has elapsed since the last time the rotating gantry encountered the marker). Based upon this rotational period and the desired number of integrations within the sector, an integration period for the sector may be determined. Thus, the integration period for respective views acquired during a first sector may be different than the integration period for respective views acquired during a second sector, for example (e.g., due to changes in the rotational period between sectors).

It may be appreciated that using a combination of synthetic triggers and physical triggers (e.g., a home marker) to trigger a data acquisition system to perform integrations on one or more detector cells may have numerous benefits. For example, the number of markers is reduced which may result in reduced manufacturing costs. Additionally, a number of integrations desired to be performed per revolution may be determined on the fly such as at install of the radiation imaging system and/or such as during an object examination (e.g., based upon a desired resolution of an image, a type of object under examination, etc.) instead of being determined during manufacturing. Moreover, inherent jitter of a sensor, such as a laser sensor or a magnetic sensor detecting the markers, and/or an error associated with such jitter may be reduced, for example.

FIG. 1 illustrates an example radiation imaging system 100. In some embodiments, the radiation imaging system 100 is configured as a computed tomography (CT) system configured to rotate a radiation source 116 and a detector array 118 about an object 104 during an examination. Although, other types of three-dimension (3D) imaging systems, such as single-photon emission computed tomography (SPECT) systems are also contemplated.

The radiation imaging system 100 comprises an examination unit 102 configured to examine objects 104, such as baggage, a bone, tissue, etc. The examination unit 102 comprises a rotating gantry 106 and a stationary gantry 108 (e.g., which may encase and/or surround at least a portion of the rotating gantry 106 (e.g., as illustrated with an outer, stationary ring, surrounding an outside edge of an inner, rotating ring)). During an examination of an object 104, the object 104 is translated into and/or through an examination region 112 (e.g., a hollow bore in the rotating gantry 106) via a support article 110, such as a conveyor belt, roller assembly, etc. While the object 104 is situated within the examination region 112, the object 104 is exposed to radiation 120.

The rotating gantry 106 may surround a portion of the examination region 112 and may comprise the radiation source 116 (e.g., an ionizing radiation source such as an x-ray source or gamma-ray source) and the detector array 118. In some embodiments, the detector array 118 is mounted on a substantially diametrically opposite side of the rotating gantry 106 relative to the radiation source 116, and during an examination of the object 104, the rotating gantry 106 (e.g., including the radiation source 116 and detector array 118) is rotated about the object 104 by a rotor 114 (e.g., belt, drive shaft, chain, roller truck, etc.). Because the radiation source 116 and the detector array 118 are mounted to the rotating gantry 106, a relative position between the detector array 118 and the radiation source 116 may be substantially maintained during the rotation of the rotating gantry 106.

During the examination of the object 104, the radiation source 116 emits cone-beam or fan-beam shaped radiation 120 from a focal spot of the radiation source 116 (e.g., a region within the radiation source 116 from which radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or multi-energy spectrums depending upon, among other things, whether the radiation imaging system 100 is configured as a single-energy system or a multi-energy (e.g., dual-energy) system.

As the emitted radiation 120 traverses the object 104, the radiation 120 may be attenuated differently by different aspects of the object 104. Because different aspects attenuate different percentages of the radiation 120, the number of photons detected by respective detector cells of the detector array 118 may vary. For example, more dense aspects of the object(s) 104, such as a bone or metal plate, may attenuate more of the radiation 120 (e.g., causing fewer photons to impinge a region of the detector array 118 shadowed by the more dense aspects) than less dense aspects, such as tissue or clothing.

Radiation detected by detector cells of the detector array 118 may be directly or indirectly converted into electrical charge, which may accumulate within the detector cell. The charge that has accumulated during an integration period may be readout by a data acquisition system 122 during an integration to generate an analog signal indicative of the incoming radiation photon flux rate at respective detector cells. The data acquisition system 122 may also be configured to convert the analog signals into digital signals. These digitals signals are typically in projection space and are, at times, referred to as projections or projection data.

The data acquisition system 122 is coupled to a triggering system 134 configured to initiate integrations at the data acquisition system 122 according to a set of triggers, which may include both markers (e.g., physical triggers or location-based triggers) and synthetic triggers (e.g., time-based triggers). The markers may be disposed on the stationary gantry 108 and/or the rotating gantry 106 and may divide a revolution into sectors (e.g., the markers divide the revolution into 18, 20° sectors). For example, the markers may include apertures, fins, or magnets disposed on the stationary gantry 108 adjacent an airgap between the rotating gantry 106 and the stationary gantry 108. The triggering system 134 may use one or more of the markers to trigger an integration, to determine a location of the rotating gantry 106 relative to the stationary gantry 108, and/or to determine a rotational period of the rotating gantry 106. The triggering system 134 may also comprise an optical sensor, magnetic sensor, or other sensor disposed on an opposite gantry 106, 108 relative to the markers. The sensor is configured to identify the markers. As will be described in more detail below, one or more of the markers may serve as a physical trigger for integrations at the data acquisition system 122.

The triggering system 134 may also comprise a timing element configured to trigger (e.g., initiate) integrations at the data acquisition system 122 responsive to an integration period having lapsed since a last integration. These time-based triggers may be referred to as synthetic triggers because these triggers are not initiated by the identification of a marker, but rather by a lapse in time. As will be described in more detail below, the triggering system 134 may adjust the integration period on the fly during a revolution based upon a collective integration time of integrations that have already occurred during the revolution and/or based upon a rotational period of the rotating gantry 106.

In some embodiments, the triggering system 134 is coupled to a terminal 126 (e.g., a workstation or computer) and information may be exchanged between the triggering system 134 and the terminal 126. In some embodiments, information transmitted to the triggering system 134 from the terminal 126 may be used to determine a desired number of integrations per revolution. For example, a user 130 may specify, at the terminal 126, a desired image resolution or other image parameter for images produced by the image generator 124 and, based upon this user specification, the triggering system 134 may determine a desired number of integrations per revolution. As still another example, the terminal 126 may, via user input or programmatically, determine the type of object under examination, and the triggering system 134 may determine the desired number of integrations per revolution based upon the type of object under examination.

The projections generated by the data acquisition system 122 may be transmitted to an image generator 124 operably coupled to the data acquisition system 122. The image generator 124 is configured to convert at least some of the data from projection space to image space using suitable analytical, iterative, and/or other reconstruction techniques (e.g., tomosynthesis reconstruction, back-projection, iterative reconstruction, etc.) and/or to compile at least some of the data to generate two-dimensional and/or three-dimensional images of the object 104.

The terminal 126 is operably coupled to the image generator 124 and is configured to receive the image(s), which can be displayed on a monitor 128 to the user 130 (e.g., security personnel, medical personnel, etc.). In this way, the user 130 can inspect the image(s) to identify areas of interest within the object(s) 104. The terminal 126 can also be configured to receive user input which can direct operations of the examination unit 102 (e.g., a speed of a conveyor belt, activation of the radiation source(s) 116, etc.).

In the example radiation imaging system 100, a controller 132 is operably coupled to the terminal 126. The controller 132 may be configured to control operations of the examination unit 102, for example. By way of example, in some embodiments, the controller 132 is configured to receive information from the terminal 126 (e.g., adjust a speed of a conveyor belt, adjust a desired rotational speed of the rotating gantry 106, etc.).

It may be appreciated that components of the radiation imaging system 100 described above are merely example components and the arrangement of such components is merely an example arrangement. Such components and/or arrangements are not intended to be interpreted in a limiting manner, such as necessarily specifying the location, inclusion, and/or relative position of the components. By way of example, in some embodiments, the data acquisition system 122 is part of the detector array 118 and/or is located on a rotating gantry 106 of the radiation imaging system 100. Further, at least some of the triggering system 134 may be located on the rotating gantry 106 (e.g., the markers may be located on the stationary gantry 108 and the sensor(s) configured to detect the markers may be located on the rotating gantry 106).

FIGS. 2A-2D provide an example technique for creating synthetic triggers to trigger the data acquisition system to perform integrations during a revolution. More particularly, starting with FIG. 2A, a gantry 201 (e.g., the rotating gantry 106 or the stationary gantry 108) is provided. The gantry 201 comprises markers 202-224 that are spaced along a rotational plane of the gantry 201. The markers 202-224 may be magnetic markers, optical markers, etc. (e.g., apertures carved within the gantry 201, fins protruding from the gantry 201, etc.). The number of markers 202-224 and/or the spacing between markers 202-224 may be design specific. For purposes of illustration, the gantry 201 comprises 12 markers spaced relatively equidistant about or along the gantry 201. However, the instant application is not intended to be limited to such an embodiment. For example, the markers 202-224 may be spaced non-uniformly about the gantry 201 and/or the number of markers 202-224 spaced along the gantry 201 may be more or less than 12.

The triggering system 134, or more specifically the markers 202-224 of the triggering system 134, may divide the gantry 201 (e.g., and thus a revolution of the rotating gantry 106) into a plurality of sectors, where a sector is defined by a starting marker and an ending marker. For example, a start of a first sector 242 is defined by a first marker 202 (e.g., a home marker) and an end of the first sector 242 (e.g., and start of a second sector) is defined by a second marker 204. As another example, a start of an eleventh sector 246 is defined by an eleventh marker 222 and an end of the eleventh sector 246 (e.g., and start of a twelfth sector 248) is defined by a twelfth marker 224. In this way, via the placement of these 12 markers 202-224 about the gantry 201, the triggering system 134 defines 254 a total of 12 sectors for the gantry 201 and thus for a revolution of the rotating gantry 106, for example.

Prior to a revolution of the rotating gantry 106, the triggering system 134 may determine 252 a desired total number of integrations for the revolution. The total number of integrations may be determined 252 based upon manufacturing parameters (e.g., the image generator 124 may be designed to receive data for a specified number of views), based upon image parameters, etc. For example, in some embodiments, a user may specify a desired image resolution for an examination and the desired number of integrations may be determined based upon the desired image resolution. As another example, a type of object under examination or to be examined may be determined (e.g., based upon user input or automated object recognition techniques) and the desired number of integrations may be determined based upon the type of object (e.g., based upon a desired image resolution for the type of object).

In the illustrated example, the triggering system 134 has determined 252 that the desired total number of integrations for a (e.g., 360 degree) revolution is 720 (e.g., the radiation imaging system 100 is to acquire 720 views during the revolution).

In some embodiments, based upon the desired total number of integrations and the position of the markers 202-224 along the gantry 201, the triggering system 134 may determine 256 a desired number of integrations to occur for each sector of the revolution. Where the markers are spaced uniformly (e.g., and thus respective sectors correspond to a same arc length), the number of integrations per sector may be based upon the desired total number of integrations and the total number of sectors. For example, the triggering system 134 may determine 256 that 60 integrations are desired to occur per sector based upon the desired total number of integrations being 720 and the numbers of sectors being 12 (e.g., 720/12=60). If the markers are not uniformly spaced over the revolution, the number of integrations per sector may be proportional to an arc length of the revolution represented by the sector, for example.

Of the 720 integrations that are desired to occur during the example revolution, a first integration may be triggered by a first marker 202, which acts as a physical trigger. The remaining 719 integrations may be triggered by synthetic markers as described above. It may be appreciated that while the foregoing example provides for assigning an equal number of integrations to respective sectors (e.g., 60 integrations per sector), in some embodiments, the number of integrations that are desired may vary on a sector-by-sector basis based upon the arc length for the sector, the position of the sector relative to the object under examination, etc.

Figure 2A:
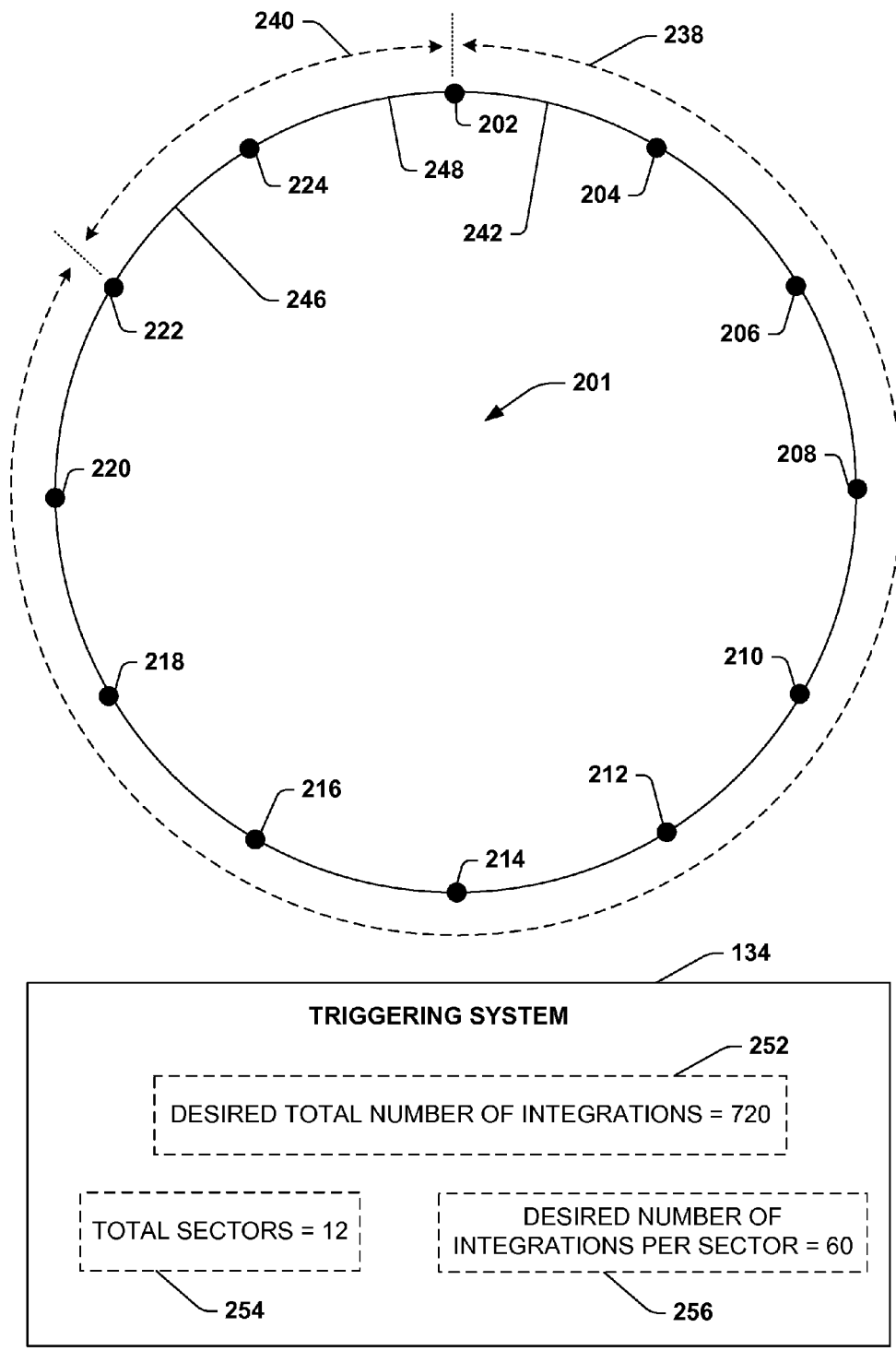
FIG. 2A illustrates example technique for creating synthetic triggers to trigger the data acquisition system to perform integrations during a revolution.
Figure 2B:
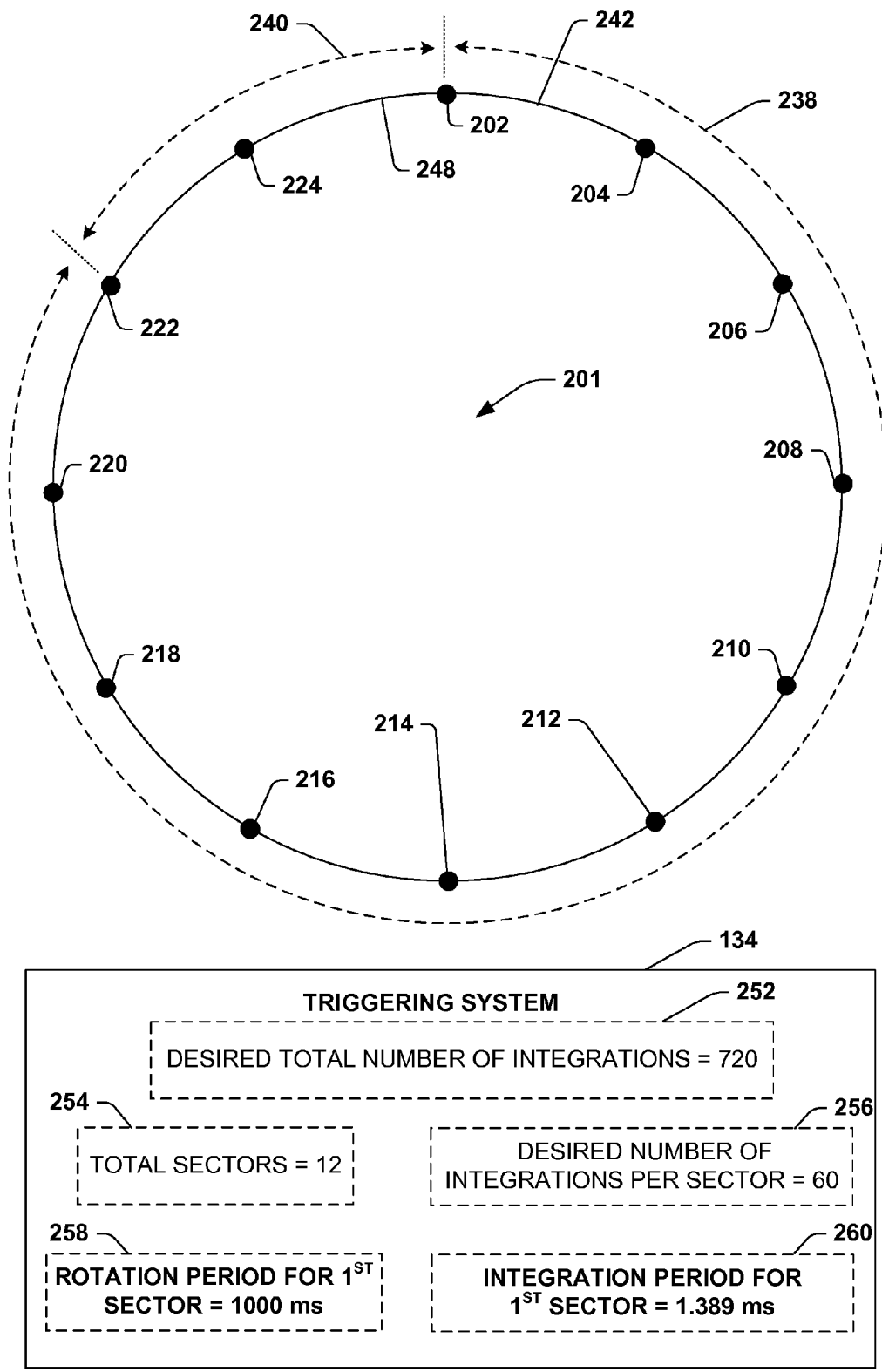
FIG. 2B illustrates example technique for creating synthetic triggers to trigger the data acquisition system to perform integrations during a revolution.

Referring to FIG. 2B, for a first set of sectors 238, an integration period for integrations to be performed within respective sectors of the first set of sectors 238 is based upon a rotational period of the rotating gantry 106 at a start of the sector. By way of example, at the start of the first sector 242, as indicated by the first marker 202, the rotational period for the first sector 242 is determined 258 (e.g., where the rotational period corresponds to the amount of time that has elapsed since the rotating gantry 106 last encountered the first marker 202). Based upon this rotational period and the number of integrations to be performed during the first sector 242, an integration period for the first sector 242 may be determined 260. For purposes of illustration, assuming the rotational period, as determined 258 from the first marker 202, is 1000 ms, assuming the arc length of the first sector 242 is approximately $1/12^{th}$ of the circumference of the revolution, and assuming 60 integrations are desired to be performed within the first sector 242 (e.g., as described with respect to FIG. 2A), the triggering system 134 determines 260 that the integration period between integrations within the first sector 242 is 1.389 ms (e.g., 1000/12/60). Thus, respective views represent 1.389 ms of the revolution.

Figure 2C:
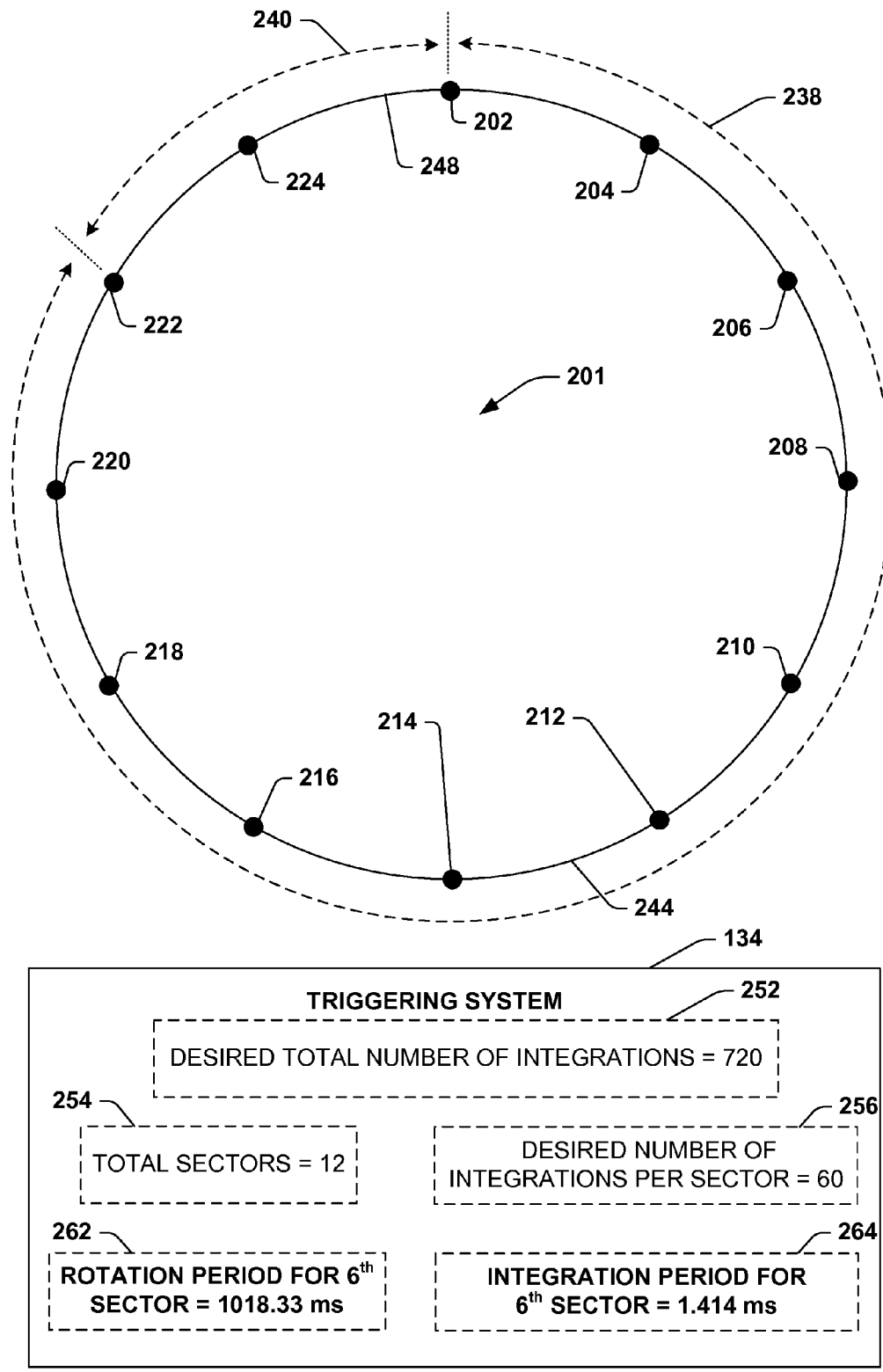
FIG. 2C illustrates example technique for creating synthetic triggers to trigger the data acquisition system to perform integrations during a revolution.

As another example, referring to FIG. 2C, at the start of the sixth sector 244, as indicated by the sixth marker 212, the rotational period for the sixth sector 244 is determined 262 (e.g., where the rotational period corresponds to the amount of time that has elapsed since the rotating gantry 106 last encountered the sixth marker 212). Based upon this rotational period and the number of integrations to be performed during the sixth sector 244, an integration period for the sixth sector 244 may be determined 264. For purposes of illustration, assuming the rotational period, as determined 262 from the sixth marker 212, is 1018.33 ms (e.g., thus indicating that the rotating gantry 106 has slowed down relative to the rotational period as determined 258 at the first marker 202), assuming the arc length of the sixth sector 244 is approximately $1/12^{th}$ of the circumference of the revolution, and assuming 60 integrations are desired to be performed within the sixth sector 244 (e.g., as described with respect to FIG. 2A), the triggering system 134 determines 264 that the integration period between integrations within the sixth sector 244 is 1.414 ms (e.g., 1018.33/12/60). Thus, respective views represent 1.414 ms of the revolution.

While the integration periods for sectors of the first set of sectors 238 merely depend upon the respective rotational period for the sector, the integration periods for a second set of sectors 240 may take other variables into account when determining the integration periods for sectors of the second set of sectors 240. By way of example, the integration periods for sectors of the second set of sectors 240 may depend upon the rotational period for the sector as well as the collective integration time for sectors of the revolution preceding the sector for which an integration period is being determined (e.g., a collective integration time for the first set of sectors 238 and any sectors of the second set of sectors 240 preceding the sector for which the integration period is being determined). Moreover, while the integration period for sectors of the first set of sectors 238 may be based upon the number of integrations to occur within the sector, in some embodiments the integration period for sectors of the second set of sectors may be based upon a number of integrations that are remaining of the desired total number of integrations.

Figure 2D:
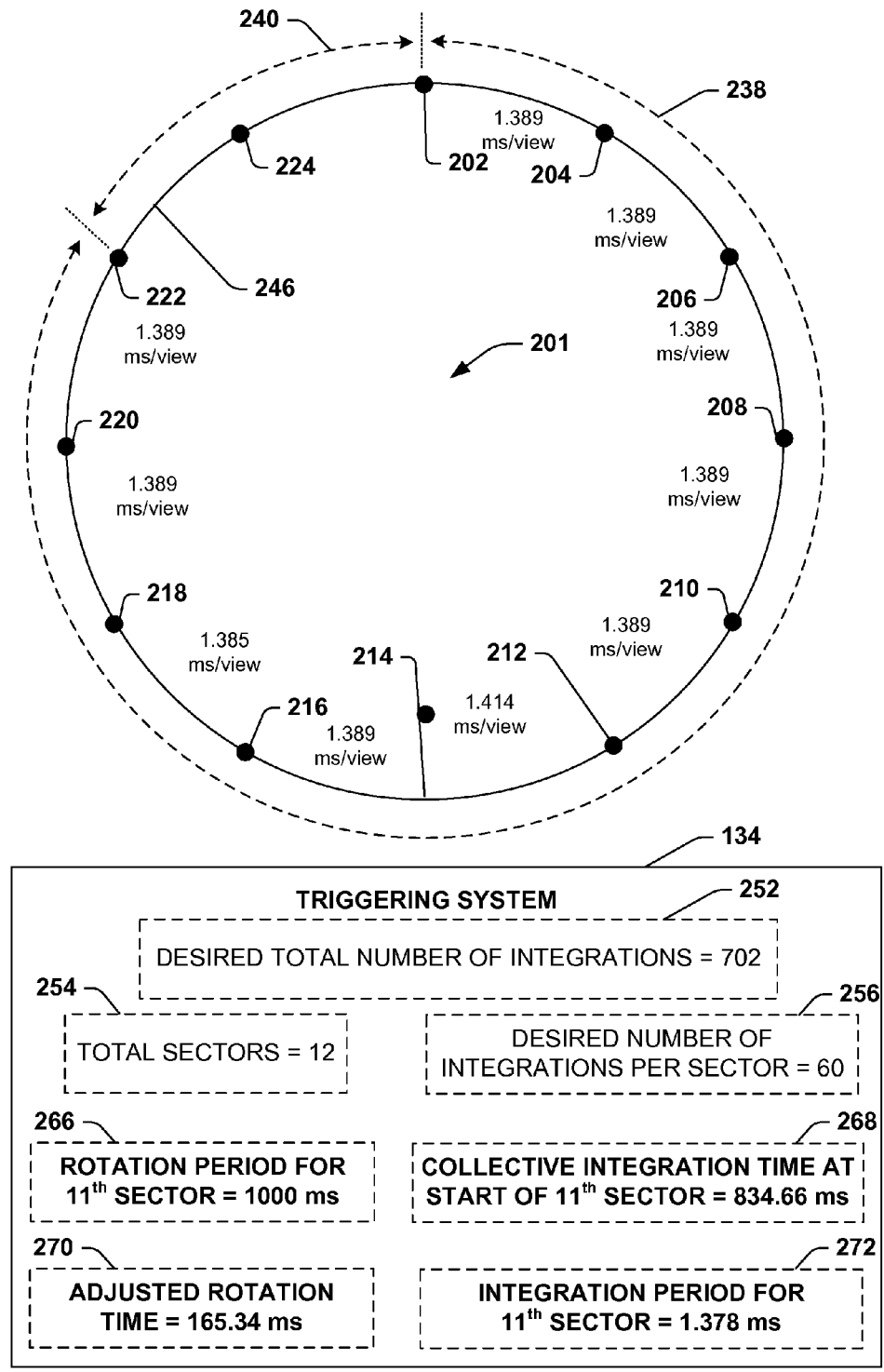
FIG. 2D illustrates example technique for creating synthetic triggers to trigger the data acquisition system to perform integrations during a revolution.
Figure 2E:
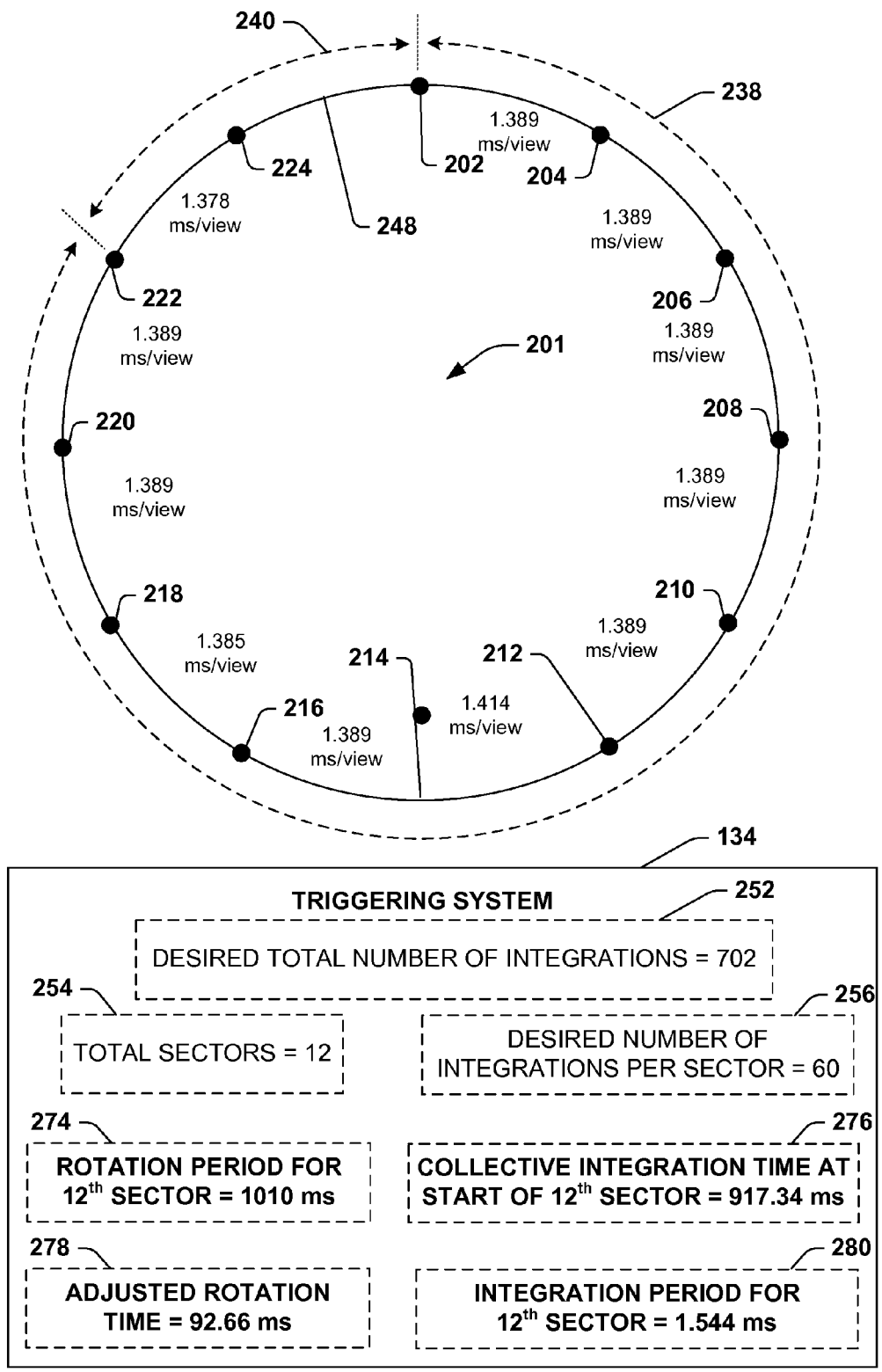
FIG. 2E illustrates example technique for creating synthetic triggers to trigger the data acquisition system to perform integrations during a revolution.

By way of example, referring to FIGS. 2D and 2E, illustrations are provided to describe how the triggering system 134 may determine a desired integration period for respective sectors of the second set of sectors 240 based upon the rotational period for the sector and a collective integration time that has accumulated for integrations occurring during previous sectors of the revolution. At the start of the eleventh sector 246 (e.g., where the start of the eleventh sector 246 is represented by the eleventh marker 222), the rotational period for the eleventh sector 246 is determined 266 (e.g., where the rotational period corresponds to the amount of time that has elapsed since the rotating gantry 106 last encountered the eleventh marker 222) and a collective integration time for the revolution at the start of the eleventh sector 246 is determined 268. The collective integration time represents a summation of the integration periods that have occurred during respective sectors of the revolution preceding the eleventh sector 246 (e.g., the collective integration time for sectors 1-10). For example, in the illustrated example, the integration period for respective sectors is listed in FIG. 2D and thus the triggering system 134 determines 268 that the collective integration time at the start of the eleventh sector is 834.66 ms (1.389*60+1.389*60+ 1.389*60+1.389*60+1.389*60+1.414*60+1.389*60+ 1.385*60+1.389*60+1.389*60).

If the rotational period, as measured at the eleventh marker 222, is 1000 ms, the triggering system 134 may determine 270 an adjusted rotation time based upon a difference between the rotational period for the eleventh sector 246 and the collective integration time at the start of the eleventh sector 246. For example, referring to FIG. 2D, the triggering system 134 may determine 270 an adjusted rotation time at the start of the eleventh marker 222 to be 165.34 ms (e.g., 1000-834.66). Using the adjusted rotation time and the number of integrations remaining at the start of the eleventh marker 222 (e.g., 120 integrations if the eleventh sector 246 and the twelfth sector 248 are each desired to perform 60 integrations), an integration period for the eleventh sector 246 may be determined 272. For example, the integration period for the eleventh sector 246 may be 1.378 ms (e.g., 165.34/120).

A process similar to that described above may be repeated for respective sectors of the second set of sectors 240. For example, referring to FIG. 2E, if the triggering system determines 274 that the rotational period for the twelfth sector 248, as measured at the twelfth marker 224, is 1010 ms and determines 276 that the collective integration time at the twelfth marker 224 is 917.34 ms, the adjusted rotation time at the start of the twelfth marker 224 may be determined 278 to be 92.66 ms (e.g., 1010-917.34). Using this adjusted rotation time and the number of integrations remaining at the start of the twelfth marker 224, an integration period for the twelfth sector 248 may be determined 280. For example, the integration period for the twelfth sector 248 may be 1.544 ms (e.g., 92.66/60).

Upon the triggering system 134 identifying the first marker 202 (e.g., a home marker), the triggering system 134 may trigger an integration to begin the revolution and may proceed to determine integration periods as described with respect to FIGS. 2A-2E for the next revolution of the rotating gantry 106.

Figure 3:
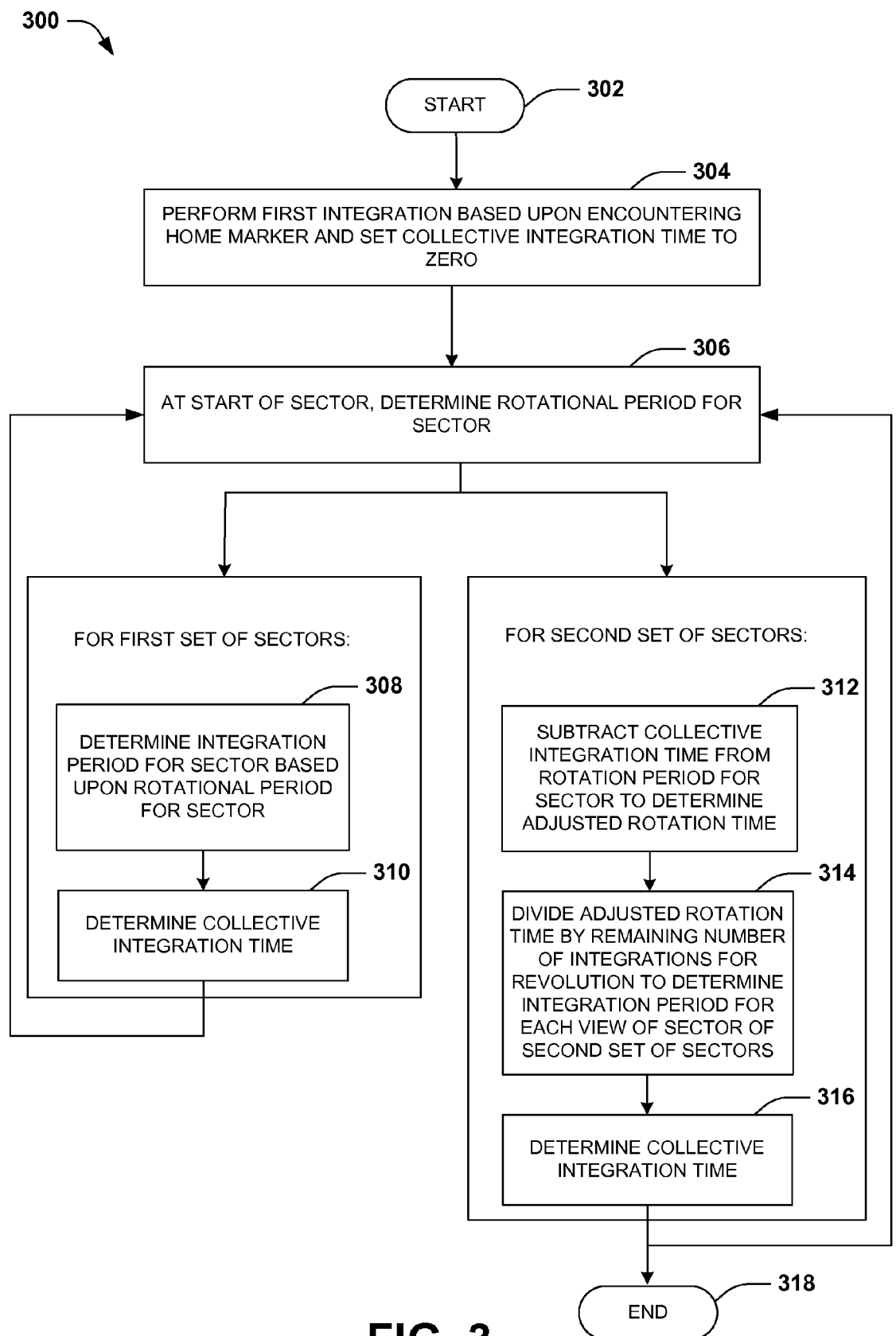
FIG. 3 is a flow diagram illustrating an example method for triggering a radiation imaging system to perform data acquisition.

Referring to FIG. 3, a flow diagram of an example method 300 for triggering a radiation imaging system (e.g., 100 in FIG. 1) to perform data acquisition is provided. It may be appreciated that for purposes of brevity, features described above that are repeated in the example method 300 are not described in detail again with respect to the example method 300.

As described with respect to FIG. 2, a revolution of a rotating gantry of the radiation imaging system may be physically divided into a plurality of sectors by markers, and the example method 300 may use these markers to determine integration periods for integrations and/or to trigger integrations. For example, in some embodiments, the first integration of a revolution may be triggered by a marker and the remaining integrations of the revolution may be triggered by a lapse in time (e.g., triggered by synthetic triggers or time-based triggers).

The example method 300 starts at 302. At 304 in the example method 300, a first integration is performed (e.g., a first view is generated) based upon encountering a home marker. A collective integration time is set to zero or some other base value responsive to encountering the home marker. In an example of performing the first integration, one or more detector cells of a radiation detector array are read out to generate one or more voltage pulses that are sampled to generate projection data of an object under examination. In an example, a second integration is triggered responsive to a time interval equivalent to a first integration period for the first sector having lapsed since the first integration. At 306 in the example method 300, rotational periods are determined for respective sectors at the start of the sector. The rotational period for a sector may be determined at a marker, designating a start of the sector. The rotational period may be based upon the time that has lapsed since the marker was last encountered, based upon an instantaneous speed of the rotating gantry as measured at the marker, or using another technique as described above.

At 308 in the example method 300, an integration period is determined for a sector at the start of the sector based upon the rotational period for the sector. For example, in some embodiments, the rotational period for the sector may be divided by a desired total number of integrations for the revolution to determine an integration period for the sector. As another example, the rotational period may be multiplied by a fraction of the revolution represented by the sector (e.g. the sector represents $1/12^{th}$ of the revolution) to get a product, which can then be divided by the desired total number of integrations to be performed within the sector (e.g., as described with respect to FIGS. 2B and 2C). At 310 in the example method 300, at an end of the sector, a collective integration time may be determined. The collective integration time may be indicative of the total integration time for the revolution based upon the integration period for the sector and the integration period for previous sectors of the revolution (e.g., as described with respect to FIG. 2D). The actions described with respect to 308 and 310 may be performed for respective sectors of a first set of sectors.

Upon completion of the first set of sectors, the example method 300 may perform a second set of actions 312-316 for respective sectors of a second set of sectors. By way of example, at 312 in the example method 300, the collective integration time at the start of a sector may be subtracted from a rotational period for the sector to determine an adjusted rotation time indicative of an expected integration time remaining. Further, at 314 the adjusted rotation time may be divided by a remaining number of integrations for the revolution to determine an integration period for the sector (e.g., as described with respect to FIGS. 2D and 2E). At 316 in the example method 300, at an end of the sector, a collective integration time may be determined. The collective integration time may be indicative of the total integration time for the revolution based upon the integration period for the sector and the integration period for previous sectors of the revolution (e.g., as described with respect to FIG. 2D). The actions described with respect to 312-316 may be performed for respective sectors of a second set of sectors.

Upon the revolution being complete (e.g., and the home marker being detected to indicate the start of a next revolution), the example method 300 ends at 318.

Figure 4:
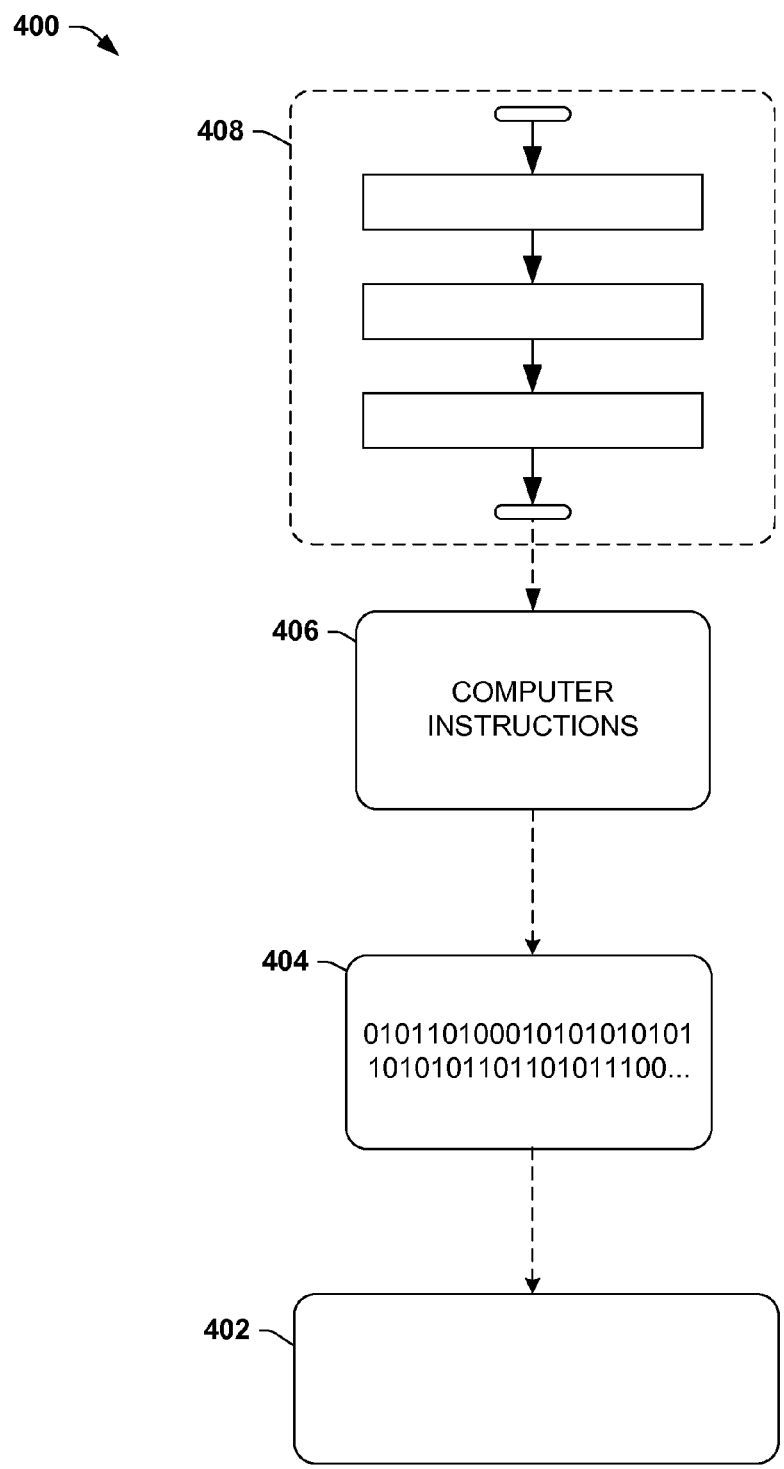
FIG. 4 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 4, wherein the implementation 400 comprises a computer-readable medium 402 (e.g., a flash drive, CD-R, DVD-R, application-specific integrated circuit (ASIC), field-programmable gate array (FPGA), a platter of a hard disk drive, etc.), on which is encoded computer-readable data 404. This computer-readable data 404 in turn comprises a set of processor-executable instructions 406 configured to operate according to one or more of the principles set forth herein. In one such embodiment 400, the processor-executable instructions 406 may be configured to perform a method 408 when executed via a processing unit, such as at least some of the example method 300 of FIG. 3. In another such embodiment, the processor-executable instructions 406 may be configured to implement a system, such as at least some of the example system 100 of FIG. 1. Many such computer-readable media may be devised by those of ordinary skill in the art that are configured to operate in accordance with one or more of the techniques presented herein. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". The claimed subject matter may be implemented as a method, apparatus, or article of manufacture (e.g., as software, firmware, hardware, or any combination thereof).

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method for triggering a radiation imaging system to perform integrations, where a revolution of a rotating gantry of the radiation imaging system is divided into a plurality of sectors, the method comprising:
   for a first sector of the revolution:
      determining a first rotational period;
      determining a first integration period based upon the first rotational period; and
      triggering one or more integrations during the first sector based upon the first integration period; and
   for a second sector of the revolution:
      determining a second rotational period;
      determining a second integration period based upon the second rotational period, the second integration period different than the first integration period; and
      triggering one or more integrations during the second sector based upon the second integration period.

2. The method of claim 1, comprising:
   determining a collective integration time based upon the first integration period and the second integration period; and
   for a third sector of the revolution:
      determining a third rotational period;
      determining a third integration period based upon the third rotational period and the collective integration time; and
      triggering one or more integrations during the third sector based upon the third integration period.

3. The method of claim 2, the determining a third integration period comprising:
   subtracting the collective integration time from the third rotational period to determine an adjusted rotation time.

4. The method of claim 3, the determining a third integration period comprising:
   dividing the adjusted rotation time by a number of integrations remaining for the revolution at a start of the third sector.

5. The method of claim 2, the determining a third integration period comprising:
   determining the third integration period based upon a number of integrations remaining for the revolution at a start of the third sector.

6. The method of claim 1, the determining a first rotational period comprising:
   determining the first rotational period at a start of the first sector, the start of the first sector indicated by a marker.

7. The method of claim 1, the triggering one or more integrations during the first sector comprising:
   triggering a first integration; and
   triggering a second integration responsive to a time interval equivalent to the first integration period having lapsed since the first integration.

8. The method of claim 1, the determining a first integration period comprising:
   determining the first integration period based upon a number of integrations desired to be performed during the first sector.

9. The method of claim 1, the determining a first rotational period comprising:
   determining the first rotational period based upon a time elapsed since a marker was traversed during a previous rotation.

10. The method of claim 1, wherein a desired number of integrations to be performed during the first sector is equal to a desired number of integrations to be performed during the second sector.

11. A method for triggering an radiation imaging system to perform data acquisition, comprising:
   determining a desired total number of integrations for a revolution of a rotating gantry;
   determining a first integration period between integrations for a sector based upon a rotational period of the rotating gantry at a start of the sector;
   at a defined location in the revolution, determining a collective integration time of integrations performed from a start of the revolution; and
   determining a second integration period between integrations for a second sector based upon the collective integration time.

12. The method of claim 11, wherein the determining a second integration period comprises:
   determining the second integration period based upon a second rotational period of the rotating gantry at a start of the second sector.

13. The method of claim 12, comprising:
   determining the second rotational period of the rotating gantry based upon a previous revolution of the rotating gantry.

14. The method of claim 12, the determining a second integration period, comprising:
   subtracting the collective integration time from the second rotational period to determine an adjusted rotation time for the second sector; and
   dividing the adjusted rotation time by a number of integrations remaining for the revolution to determine the second integration period.

15. The method of claim 11, comprising:
   for the sector of the revolution:
      identifying a marker indicating the start of the sector; and
      performing a first integration after a first timespan has elapsed from identifying the marker, the first timespan equal to the first integration period.

16. The method of claim 15, the performing a first integration comprising:
   reading out one or more detector cells of a radiation detector array to generate one or more voltage pulses; and
   sampling the one or more voltage pulses to generate projection data.

17. The method of claim 11, the determining a second integration period, comprising:
   determining the second integration period based upon a number of integrations remaining for the revolution.

18. A radiation imaging system, comprising:
   a radiation source;
   a detector array comprising one or more detector cells configured to accumulate charge generated responsive to impinging radiation emitted by the radiation source;
   a rotating gantry configured to rotate the radiation source and the detector array; and
   a data acquisition system configured to integrate the charge that has accumulated during a view, where an integration period between integrations is adjusted during a revolution of the rotating gantry based upon:
      a number of integrations remaining to be performed; and
      a collective integration time of integrations performed during a first portion of the revolution.

19. The radiation imaging system of claim 18, comprising:
   a position tracking system configured to divide the revolution into a plurality of sectors, where a plurality of integrations are performed per sector.

20. The radiation imaging system of claim 19, comprising:
   a stationary gantry, and
   the position tracking system comprising one or more markers located on the stationary gantry or the rotating gantry, the markers comprising at least one of magnetic markers or optical markers.

* * * * *

UNITED STATES PATENT AND TRADEMARK OFFICE
CERTIFICATE OF CORRECTION

PATENT NO. : 9,869,646 B2  
APPLICATION NO. : 14/682461  
DATED : January 16, 2018  
INVENTOR(S) : Zoboyan et al.

Page 1 of 1

It is certified that error appears in the above-identified patent and that said Letters Patent is hereby corrected as shown below:

On the Title Page

Abstract (57), Line 6: Delete the word "configure" and insert the word --configured--

Signed and Sealed this
Twelfth Day of June, 2018

Andrei Iancu
*Director of the United States Patent and Trademark Office*